United States Patent [19]

Baserga

[11] Patent Number: 5,262,308
[45] Date of Patent: Nov. 16, 1993

[54] CELL LINES WHICH CONSTITUTIVELY EXPRESS IGF-1 AND IGF-1 R

[75] Inventor: Renato Baserga, Ardmore, Pa.

[73] Assignee: Thomas Jefferson University, Philadelphia, Pa.

[21] Appl. No.: 827,690

[22] Filed: Jan. 28, 1992

[51] Int. Cl.$^5$ .................. C12N 15/00; C12N 5/10
[52] U.S. Cl. ........................ 435/69.1; 435/172.3; 435/240.2; 435/320.1; 435/69.1
[58] Field of Search ............... 435/172.3, 240.2, 320.1, 435/252.3, 69.1

[56] References Cited

PUBLICATIONS

Pietrzkowski, Z. et al., *Mol Cell. Biol.*, 12(9):3883–89, Sep. 1992.
Pietrzkowski, Z. et al. *Fed. Am. Soc. Exp. Biol. (FASEB)*, 5(6):A1622, Apr. 21–25, 1991.
Armelin et al., *Nature* (London), 310:655–60 (1984).
Arteaga et al., *Proc. Natl. Acad. Sci. USA*, in press (1991).
Cherington et al., *Proc. Natl. Acad. Sci.*, 76:3937–41 (1979).
Chomczynski and Sacchi, *Anal. Biochem.*, 162:156–159 (1987).
Feinberg and Vogelstein, *Anal. Biochem.*, 132:6–13 (1983).
Foekens et al., *Cancer Res.*, 49:5823–8 (1989).
Gammeltoft et al., *Cancer Res.*, 48:1233–7 (1988).
Gai et al., *Oncogene Res.*, 3:377–86 (1988).
Gritz and Davies, *J. Gene*, 25: 179–188 (1983).
Goldring and Goldring, *Eucar. Gene Express*, 1:301–326 (1991).
Hartman et al., *Leukemia*, 2:241–4 (1988).
Hizuka et al., *Endocrinol. Japon*, 34:81–88 (1987).
Jaskulski et al., *Science*, 240:1544–1546 (1988).
Kaczmarek et al., *Science*, 228:1313–5 (1985).
Kaczmarek et al., *Cell Biol. Int. Rept.*, 10:455–63 (1986).
Kaleko et al., *Mol. Cell Biol.*, 10:464–473 (1990).
Kiefer et al., *Exp. Cell Res.*, 184:396–406 (1989).
Kozak et al., *Cell Immunol.*, 1009–318–331 (1987).
Lammers et al., *J. Biol. Chem.*, 265:16886–16890 (1990).
Lammers et al., *EMBO J.*, 8:1369–1375 (1989).
Laemmli, U.K., *Nature*, 227:680–685 (1970).
Lee et al., *J. Clin. Endocrinol. & Metabol.*, 62:28–35 (1986).
Lin and Lee, *Proc. Natl. Acad. Sci.*, 81:988–992 (1984).
Leof et al., *Exp. Cell Res*, 141:107–15 (1982).
Minuto et al., *Cancer Res.*, 48:3716–9 (1988).
Nakanishi et al., *J. Clin. Invest.*, 82:354–9 (1988).
Ota et al., *Molec. Brain Res.*, 6:69–76 (1989).
Ota et al., *Eur. J. Biochem.*, 174:521–30 (1988).
Phillips et al., *Exp. Cell Res.*, 175:396–403 (1988).
Phillips et al., *J. Cell Physiol.*, 133:135–143 (1987).
Praeger et al., *In Vitro*, 22:355–9 (1986).
Pepe et al., *J. Cell Physiol.*, 133:219–227 (1984).
Pekonen et al., *Cancer Res.*, 48:1343–7 (1988).
Pekonen et al,. *Int. J. Cancer*, 43:1029–33 (1989).
Peyrat et al., *Cancer Res.*, 48:6429–33 (1988).
Ritvos et al, *Endrocrinology*, 122:395–401 (1988).
Russell et al., *Proc. Natl. Acad. Sci. USA*, 81:2389–92 (1984).
Stewart et al., *J. Biol. Chem.*, 265:21172–8 (1990).
Stracke et al., *J. Biol. Chem.*, 264:21544–9 (1989).
Scher et al., *Biochem. Biophys. Acta*, 560:217–41 (1979).
Stiles et al., *Proc. Natl. Acad. Sci. USA*, 76:1279–83 (1979).
Shen et al., *Mol. Cell Biol.*, 2:1145–1154 (1982).
Stoscheck and Carpenter, *Arch. Biochem. Biophys.*, 227:457–468 (1983).
Travali et al., *Mol. Cell Biol.*, 11:731–736 (1991).
Talavera et al., *J. Cancer Res.*, 50:3019–24 (1990).
Thomas, P. S., *Methods Enzymol.*, 100:255–266 (1983).
Ullrich et al., *EMBO J.*, 5:2503–2512 (1986).
Van Wyk et al., *The Biology of Normal Human Growth*, pp. 223–239, Raven Press, NY (1981).
Werner et al., *Proc. Nat. Acad. Sci. USA*, 86:7451–5 (1989).

Primary Examiner—Robert J. Hill, Jr.
Assistant Examiner—Marianne Porta Allen
Attorney, Agent, or Firm—Woodcock Washburn Kurtz Mackiewicz & Norris

[57] ABSTRACT

Cells which constitutively express IGF-1 and IGF-1 R cDNAs are provided. These cells are useful for the production of selected proteins. Methods for producing the cells are also provided. Diagnostic and therapeutic methods are provided using cells transfected with IGF-1 R.

3 Claims, 4 Drawing Sheets

FIG. I
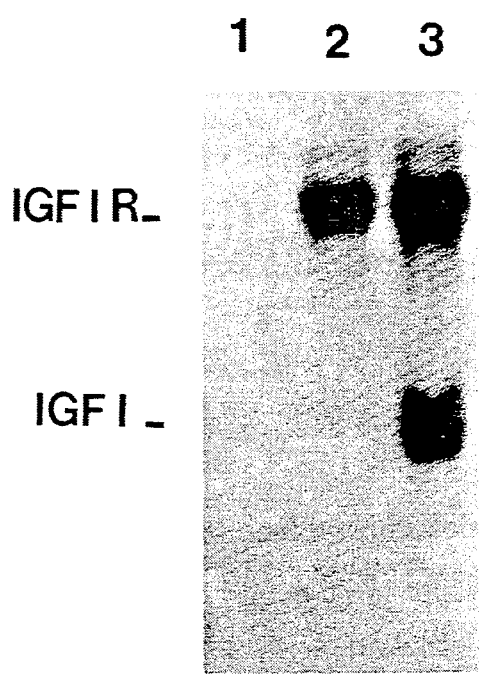

CELL LINES WHICH CONSTITUTIVELY EXPRESS IGF-1 AND IGF-1 R

INTRODUCTION

The invention was made in the course of research supported by the National Institutes of Health. The U.S. Government may have certain rights in this invention.

BACKGROUND OF THE INVENTION

The interaction of Insulin-like Growth Factor—1 (IGF-1) with its own receptor (IGF-1 R) seems to play a major role in normal development and in the control of both normal and abnormal growth. In growth hormone disturbances of growth as, for instance, in acromegalics and in patients with growth hormone deficiency, clinical assessments of disease activity correlate far better with blood levels of IGF-1 than they do with growth hormone concentrations, Van Wyk et al., *The Biology of Normal Human Growth*, pp. 223–239, Raven Press, N.Y. (1981). Werner et al., *Proc. Nat. Acad. Sci. USA*, 86:7451–5 (1989) have shown that the mRNA levels for the IGF-1 R decrease steadily in all tissues during post-natal development, reaching a maximum during the perinatal stages. IGF-1 mRNA, instead, is not so tightly regulated during development as the mRNA for the IGF-1 R, and actually reaches maximum expression in the adult liver, which is the main site of production of IGF-1. Apart from these general considerations, a number of reports have appeared indicating that the interaction of IGF-1 with its own receptor may play a major role in cell growth. For instance, IGF-1 receptors are present in phytohemagglutinin activated T lymphocytes, Kozak et al., *Cell Immunol*, 1009 318-331 (1987) and in K562 cells that are a human erythroleukemia cell line, Hizuka et al., *Endocrinol. Japon*, 34:81–88 (1987). In fact, K562 cells grow vigorously in SFM containing only IGF-1 or supraphysiological concentrations of insulin. An abundance of IGF-1 receptors has also been reported in lymphoblasts of human T cell leukemias, Lee et al., *J. Clin. Endocrinol. & Metabol.*, 62:28–35 (1986), and in HL60 cells, Pepe et al., *J. Cell Physiol.*, 133:219–227 (1987). In our own laboratory, we have been able to show that the mRNA for the IGF-1 receptor is over-expressed in HL60 cells. Again, HL60 cells, as well as other cell lines, grow well in serum-free medium containing only insulin in supraphysiological concentrations. In Burkitt cells, the number of IGF-1 receptors increase between $G_1$ and S-3 phase, Hartman et al., *Leukemia*, 2:241–4 (1988). Stem cells and progenitor cells also seem to require IGF-1 for growth. Goldring and Goldring, *Eucar. Gene Express*, 1:-301–326 (1991), list several references indicating that IGF-1 increases the proliferation of keratinocytes, smooth muscle cells, osteoblasts, chrondrocyts and neuronal cells (see their Table 4). The IGF-1 R is induced by estrogens in breast cancer cell lines, Stewart et al., *J. Biol. Chem.*, 265:21172–8 (1990), Pekonen et al., *Cancer Res.*, 48:1343–7 (1988), Peyrat et al., *Cancer Res.*, 48:6429–33 (1988), Foekens et al., *Cancer Res,,* 49:5823–8 (1989), and the expression of IGF-1 receptors seems to correlate with the growth of breast cancer, at least just as well as the estrogen receptors or the EGF receptor. Other tumors in which an increased expression of IGF-1 R or, at least, IGF-1 binding sites, have been reported include small cell lung cancer, Kiefer et al., *Exp. Cell Res.*, 184:396–406 (1989), Minuto et al., *Cancer Res.*, 48:3716–9 (1988), Nakanishi et al., *J. Clin. Invest.*, 82:354–9 (1988), choriocarcinoma cells, Ritvos et al., *Endocrinology*, 122:395–401 (1988), malignant glioma, Gammeltoft et al., *Cancer Res.*, 48:1233–7 (1988), renal carcinoma, Pekonen et al., *Int. J. Cancer*, 43:1029–33 (1989), and neoplastic human endometrium, Talavera et al., *J. Cancer Res.*, 50:3019–24 (1990). A role of the IGF-1 R in growth has also been reported in human melanoma cells, Stracke et al., *J. Biol. Chem.*, 264:21544–9 (1989), and in tumors of neural origins like neuroblastomas or pheochromocytomas, Ota et al., *Molec. Brain Res.*, 6:69–76 (1989) and Ota et al., *Cur. J. Biochem.*, 174:521–30 (1988). However, the best evidence that the IGF-1 R plays a major role in the control of cellular proliferation comes from studies with fibroblasts in cell cultures.

It has been known for a long time that IGF-1 is necessary for the growth of fibroblasts in vitro. Prototypes for growth studies have been the 3T3 mouse cells and the WI38 human diploid fibroblasts. With BALB/c3T3 cells, at least two poor plasma (ppp), are both necessary for sustained growth, Scher et al., *Biochem. Biophys. Acta*, 560:217–41 (1979). PPP can be replaced by IGF-1, or by insulin at high concentrations, but IGF-1 only (without PDGF) does not stimulate the growth of 3T3 or WI-38 cells, Stiles et al., *Proc. Natl. Acad. Sci. USA*, 76:1279–83 (1979), Leof et al., *Exp. Cell Res.*, 141:107–15 (1982), Russell et al., *Proc. Natl. Acad. Sci. USA*, 81:2389–92 (1984), Gai et al., *Oncogene Res.*, 3:377–86 (1988). Other cell lines, as for instance BHK cells, Cherington et al., *Proc. Natl. Acad.. Sci.*, 76:3937–41 (1979), and WI38 human diploid fibroblasts, Phillips et al., *Exp. Cell Res.*, 175:396–403 (1988), also require more than one growth factor for optimal growth in culture, usually PDGF (or EGF) and IGF-1. PDGF and/or EGF can actually be replaced but, until now, IGF-1 has not been replaced. For instance, PDGF can be replaced by an overexpressed c-myc, Armelin et al., *Nature* (London), 310:655–60 (1984) and Kaczmarek et al., *Science*, 228:1313–5 (1985), or even, under certain circumstances, by exposure to cycloheximide, Kaczmarek et al., *Cell Biol. Int. Rept.*, 10:455–63 (1986), and in WI38 EGF and/or PDGF can be replaced by high concentrations of calcium, Praeger et al., *In Vitro*, 22:355–9 (1986). Travali et al., *Mol. Cell Biol.*, 11:731–736 (1991), disclose that IGF-1 can be replaced by a constitutively expressed c-myb. However, it was found that in cells constitutively expressing c-myb, there was a marked increase in IGF-1 mRNA and IGF-1 secretion so that at least in this instance, although myb can replace IGF-1, it does so by simply stimulating the production of IGF-1.

The fact that these cells respond to IGF-1 plus PDGF may make 3T3 or WI38 cells sensitive to IGF-1 simply by increasing the number of IGF-1 binding sites. It has been shown that the addition of PDGF and/or EGF to BALB/c3T3 cells or to WI38 human diploid fibroblasts, increases both the production of IGF-1 and the number of IGF-1 binding sites. However, until the present invention, it was not known that the constitutive expression of IGF-1 and IGF-1 R could abrogate *all requirements* for exogenous growth factors.

SUMMARY OF THE INVENTION

Cells which constitutively express Insulin-like Growth Factor-1 (IGF-1) and its receptor, IGF-1 R, allow growth of cells in serum free media without the addition of exogenous growth factors that are required by the parent cell line. BALB/c3T3, CHO and tk-ts13 cell lines (derived from BHK cells) have been produced. These cells can be transfected with a recombinant DNA molecule encoding a selected heterologous protein under the control of a suitable expression control sequence and then cultured under suitable conditions to produce a selected protein. Large quantities of both intracellular and secreted proteins can be produced and purified from these cells.

Cells are transfected with a human IGF-1 receptor expression plasmid containing a full-length IGF-1 R cDNA under transcriptional control of a viral promoter and a selectable marker, such as an antibiotic-resistance gene. The clones produced are then transfected with an IGF-1 cDNA expression vector plus a selectable marker to obtain cell lines expressing both IGF-1 and IGF-1 R. These cell lines can be used for the production of biological products, for instance, growth factors, antigens and other protein products. The advantage of using these cells is that the various biological products are properly phosphorylated and glycosylated. In addition, since the cells are in serum-free medium, purification of the secreted proteins is made much easier. The abrogation of requirements for exogenous growth factors also makes these cell lines economically attractive. In addition, cells transfected with IGF-1 R cDNA only can be used to test for the presence of IGF-1 or for competitors of IGF-1.

DESCRIPTION OF THE DRAWINGS

FIG. 1 is an RNA blot of 3T3 cells transfected with IGF-1 and IGF-1 receptor cDNA's. BALB/c3T3 cells were transfected with human IGF-1 R cDNA, or with both IGF-1 R and the IGF-1 cDNA's and with a selectable marker. Cell lines carrying stably integrated plasmids were selected and the RNA was extracted from these cell lines. The blot was hybridized to human IGF-1 and IGF-1 receptor probes. Lane 1, BALB/c3T3 cells. Lane 2, cells carrying only the IGF-1 R plasmid (p6). Lane 3, cells transfected with both IGF-I and IGF-1 receptor plasmids (p12 cells).

FIG. 2, A and B, show the Scatchard plot analysis of IGF-1 binding sites for BALB/c3T3 cells (FIG. 2A), and p6 cells (FIG. 2B). The number of IGF-1 binding sites was determined using $I^{125}$-IGF-1. The number of IGF-1 receptors in quiescent BALB/c3T3 cells was low (~8,000 per cell.

DETAILED DESCRIPTION OF THE INVENTION

Figure 3:
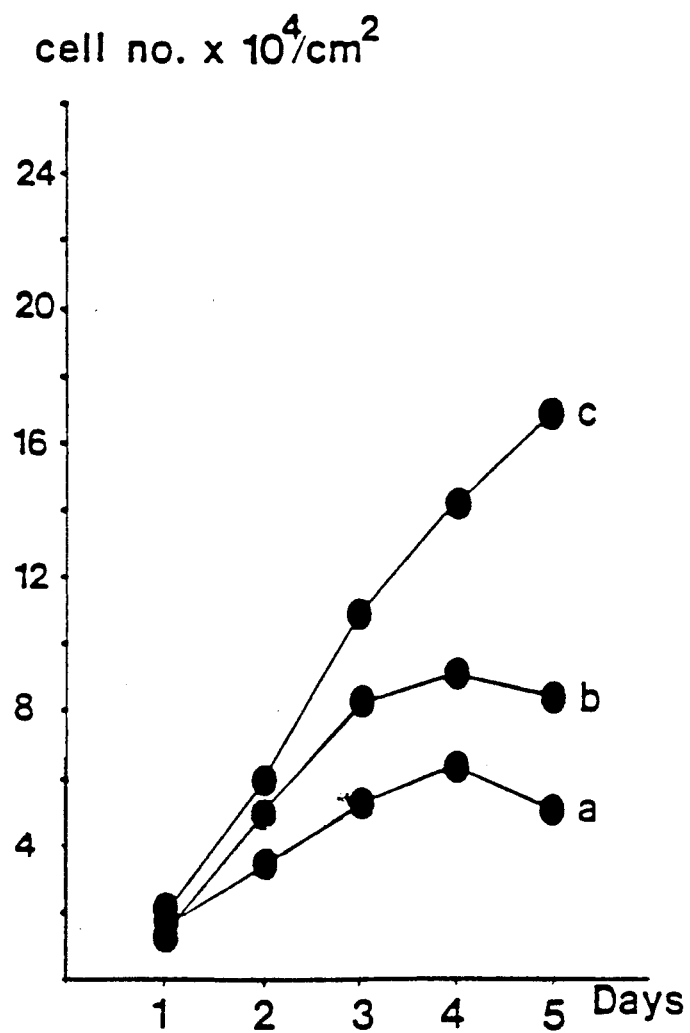
FIG. 3 is a graph showing growth of CHO cells in serum-free medium. The cell line used was CHO cells that are of Chinese hamster origin. This cell line was transfected with IGF-1 receptor, or with both IGF-1 and IGF-1 receptor cDNA's, plus a selectable marker. Curve a is the parent cell line, CHO cells. Curve b are cells transfected only with IGF-1 receptor cDNA, and curve c, cells transfected with both IGF-1 receptor and IGF-1 cDNA's.

We have discovered that cells carrying constitutively expressed IGF-1 and IGF-1 R cDNA's can grow in serum-free medium without the addition of any exogenous growth factor. This has been shown to be true for a number of cell lines, including BALB/c3T3 cells, tk-ts13 cells and CHO cells, (FIGS. 1 and 3).

In the present invention, the cells are transfected with a human IGF-1 receptor expression plasmid containing a full-length IGF-1 R cDNA under transcriptional control of a viral promoter, such as the SV40 or cytomegalovirus promoter, and a selectable marker, such as an antibiotic-resistance gene. Examples of antibiotic-resistance genes include neomycin-, puromycin-, or hygromycin-resistance genes. The clones produced are then transfected with an IGF-1 cDNA expression vector and a selectable marker to obtain cell lines expressing IGF-1 and IGF-1 R.

The cell lines of the invention can be used for the production of biological products such as growth factors, antigens and other protein products. These cells which constitutively express IGF-1 and IGF-1 R can be transfected with a recombinant DNA molecule encoding the selected heterologous protein under the control of a suitable expression control sequence. When cultured under suitable conditions, large quantities of both intracellular and secreted proteins can be produced and purified from the cells by methods known in the art. The advantage of using the cells of the invention is that the biological products are properly phosphorylated and glycosylated. The lack of requirements for exogenous growth factors also makes these cell lines economically attractive.

It was also found that the SV40 promoter is dramatically induced when the cells are grown at a temperature of at least 39.6° C. tk-ts13 cells, a temperature sensitive mutant derived from BHK cells of Syrian hamster origin, were induced to produce large amounts of proteins by increasing the culture temperature to 39.6° C. When an expression plasmid, in which the SV40 promoter directs the transcription of a reporter gene, is introduced into tk-ts13 cells, it is expressed at normal levels at the permissive temperature of 36° C. Upon shifting to 39.6° C., the SV40 promoter is superactivated, producing 40-50 times the amount of the desired RNA, and 100 times the amount of the desired protein.

This strategy (tk-ts13 cells at 39.6° C. and a construct in which the SV40 promoter directs the transcription of the desired gene or cDNA) can, therefore, be used to produce large quantities of a specific protein in mammalian cells. The levels of both RNA and protein expression reach a maximum within 20 hours upon temperature shift. The method can be used to produce and purify both intracellular and secreted proteins.

Cells transfected only with IGF-1 R cDNA can also be used to screen for the presence of IGF-1 or for competitors of IGF-1. For example, cells can be exposed to a potential competitor of IGF-1 and cell growth observed. We have found that BALB/c3T3 cells transfected only with IGF-1 R cDNA do not grow. However, they grow vigorously when incubated with either IGF-1 or insulin. The concentration of insulin, 20 μg/ml, used in these experiments is believed to be mimicking the addition of IGF-1.

It in known that overexpression of IGF-1 R cDNA in NIH 3T3 cells results in a transformed phenotype when the cells are grown in the presence of IGF-1 (Kaleko et al., *Mol. Cell Biol.*, 10:464–473 (1990)). However, in these experiments the cells were grown in serum-supplemented medium; in our experiments, serum was omitted when the medium was supplemented with IGF-1, and although our p6 cells grew under these conditions, they did not acquire the morphological phenotype of transformed cells. The role of IGF-1 R overexpression in the growth of our cell lines was demonstrated by two different experiments: 1) various clones were obtained expressing either the IGF-1 R only, (p6) or both IGF-1 and IGF-1 R (p12 cells) cDNA's, and all these clones grew in serum-free medium or, when transfected with the IGF-1 R only expression plasmid, in serum-free medium plus IGF-1. We never observed growth of BALB/c3T3 cells, the parent cell line, in serum-free medium even in the presence of IGF-1; 2). Addition of anti-sense deoxyoligonucleotides to IGF-1 R RNA inhibited the growth of p6 cells stimulated by IGF-1. Antibody to the IGF-1 R also inhibited the growth of IGF-1 stimulated p6 cells by about 40%.

From a practical point of view, these experiments show that the constitutive expression of IGF-1 and IGF-1 R allows the growth of cells in a medium totally devoid of exogenous growth factors. The ability of cells constitutively overexpressing IGF-1 and IGF-1 R to grow in serum-free medium indicates that IGF-1 and IGF-1 R interaction can be sufficient for the growth of these cells. This is further confirmed by the fact that cells overexpressing IGF-1 R only will not grow in serum-free medium, but will grow in the presence of IGF-1, or insulin, at appropriate concentrations. Under these conditions, no platelet derived growth factor (PDGF), or epidermal growth factor (EGF) are added, although these two growth factors are required for the optimal growth of the parent cell lines. We could not detect any PDGF-like activity in the conditioned medium of p12 cells or of IGF-1 stimulated p6 cells. We cannot exclude that other growth factors (known or unknown) may be involved, but we can state that whatever growth factors are needed for the growth of the parent cell line, are not present in the conditioned medium of p6 or p12 cells. Furthermore, our experiments indicate that the EGF receptor and phospholipase C$\gamma$1 are not phosphorylated when p6 cells are stimulated with IGF-1, although they are phosphorylated when stimulated with EGF or PDGF, respectively. It seems, therefore, that in our cells, the IGF-1 mediated growth is independent of the activation of the EGF or PDGF receptors.

One question raised by these experiments, therefore, is simply whether the only ligand-receptor system that is needed for the growth of cells, is the IGF-1/IGF-1 R combination and, as a corollary, that other growth factors, such as PDGF and EGF are not essential for growth under these conditions. If this were true one would have to hypothesize that the only function of PDGF and/or EGF, is simply to induce enough IGF-1 and IGF-1 R proteins to elicit the growth response. This hypothesis is only partially supported by reports already in the literature indicating that the addition of PDGF, and/or EGF, to BALB/c3T3 cells and to WI-38 human diploid fibroblasts, increase both the production of IGF-1 and the number of binding sites for IGF-1.

As an alternative explanation, it has been shown recently that there is transphosphorylation between different receptors, i.e., that, for instance, an insulin receptor can transphosphorylate EGF receptor cytoplasmic sequences, Lammers et al., *J. Biol. Chem.*, 265:16886-16890 (1990). It may therefore be possible that in our p6 and p12 cells, that express high numbers of IGF-1 receptors, the activation of these receptors by IGF-1, or insulin, may induce transphosphorylation of the PDGF and/or EGF receptors. In this respect, it should be noted that the number of IGF-1 binding sites in p6 cells is quite high, about five times the number in the parent cell line. When BALB/c3T3 cells, or WI-38 cells, are stimulated with PDGF and/or EGF, the increase in the number of binding sites of IGF-1 is only, roughly a doubling. It is, therefore, conceivable that the high number of IGF-1 binding sites in p6 and p12 cells, may result in the transphosphorylation of other receptors, for other growth factors. However, our results do not favor this explanation.

Another alternative is that the entry of fibroblasts into S phase may simply depend on the total number of growth factors' receptors activated, regardless of the type. According to this hypothesis, a sufficiently high number of receptors for any one of the three growth factors (EGF, PDGF, IGF-1) should be enough for entry into S.

Regardless of which one of the mechanisms discussed above will turn out to be the correct one, these experiments point out how crucial is the number of IGF-1 binding sites in determining the response of cells to growth factors. BALB/c3T3 cells do not respond to IGF-1 alone. On the other hand, p6 cells that differ from BALB/c3T3 cells only in the number of their IGF-1 binding sites, respond to both IGF-1 or insulin. The number of binding sites in our BALB/c3T3 cells is much lower than reported elsewhere. This may reflect a difference in cell type (BALB/c vs. NIH 3T3) or in the method used to determine binding sites, or in the amount of IGF-1 binding proteins present. With our method, the latter ones were not detected. IGF-1 is present in platelet poor plasma but BALB/c3T3 cells are not stimulated by platelet poor plasma, just as they are not stimulated by IGF-1 only. It seems, therefore, that the important element of this ligand-receptor combination is actually the receptor and, specifically, the number of receptors. The minimum number of binding sites that have to be reached to make the BALB/c3T3 cells responsive to IGF-1 only is not known.

Cell lines derived from BALB/c3T3 cells were established by transfection of a human IGF-1 receptor expression plasmid, which contained, in addition to a full-length IGF-1 R cDNA under transcriptional control by the SV40 early promoter, a selectable marker, the bacterial neomycin-resistance gene. All G418-resistant clones obtained, designated p6, behaved similarly, but more detailed experiments were carried out with a single clone. In a second round, a clone of p6 cells were transfected with an IGF-1 cDNA expression vector plus the hygromycin resistance gene, Gritz and Davies, *J. Gene,* 25: 179-188 (1983), to obtain cell lines expressing both IGF-1 and IGF-1 R. The resulting cell lines, designated p12, were used in subsequent experiments.

FIG. 1 shows a Northern blot analysis of 3T3 cell RNA and RNA from representative clones of transfected cell lines p6 and p12. In each case, the cells were in exponential growth when RNA was extracted. The blot was hybridized with the IGF-1 and IGF-1 R cDNA probes. Neither IGF-1 nor IGF-1 R mRNAs were detectable under these conditions in the parental BALB/c3T3 cells (lane 1), although both would become detectable after prolonged autoradiographic exposure. However, in p12 and p6 cells, an RNA was detected (lanes 2 and 3) of about 4.2 kb which is the size expected from the transcription of the IGF-1 R expression plasmid. IGF-1 mRNA was detectable only in p12 cells (lane 3). The blots were also hybridized to a 3A10 probe, Jaskulski et al., *Science,* 240:1544-1546 (1988), which is expressed at constant levels throughout the cell cycle. This probe was used to monitor the amounts of RNA in each lane, which proved to be roughly the same in all lanes.

Figure 2A:
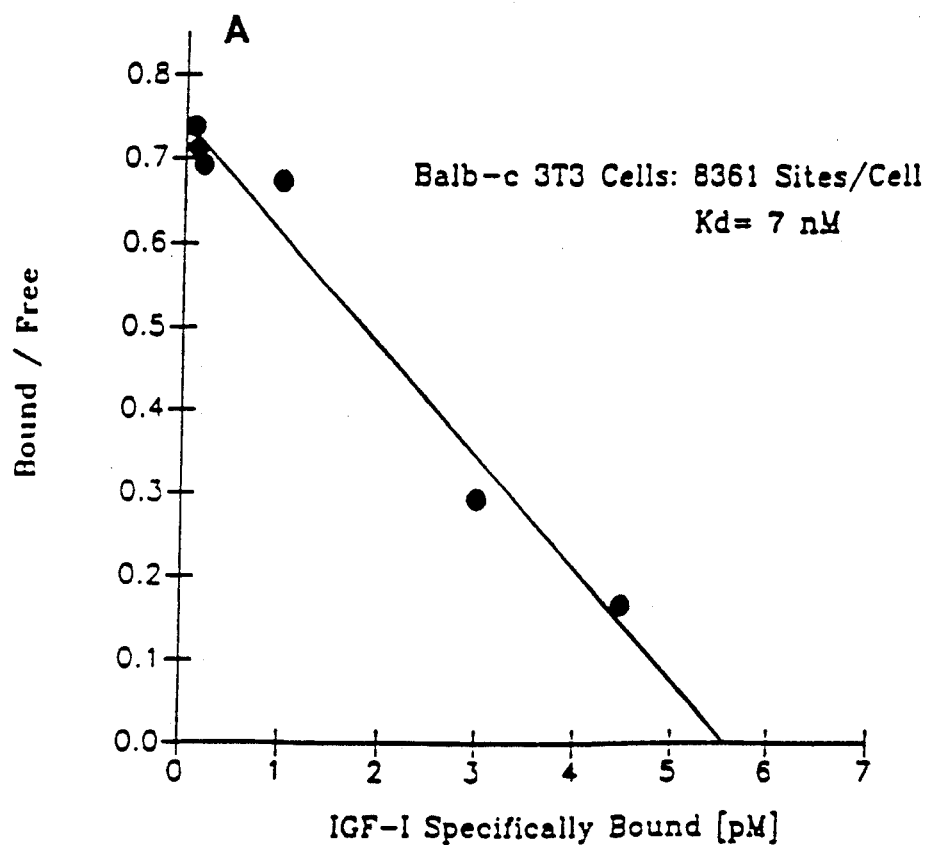
FIG. 2A), which a high level of IGF-1 binding sites was observed in p6 cells (~43,000 per cell.
Figure 2B:
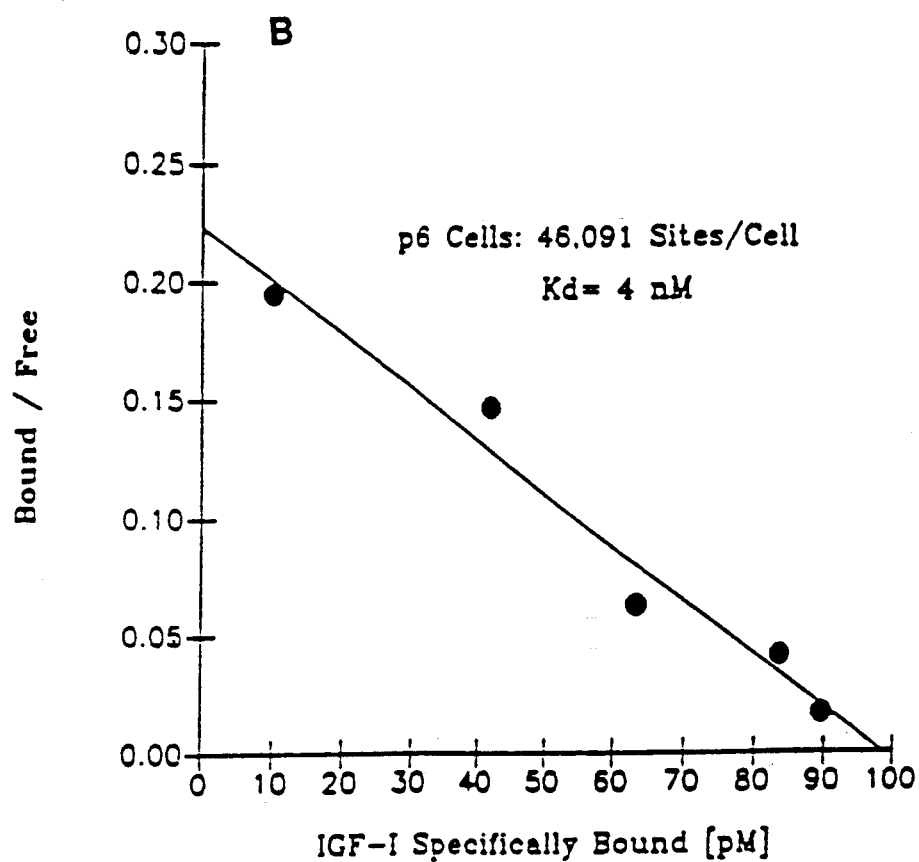
FIG. 2B).

The number of IGF-1 binding sites in p6 cells was calculated as described by Phillips et al., *J. Cell Physiol.*, 133:135-143 (1987), using $I^{125}$-IGF-1. FIG. 2 shows the Scatchard plot analysis of binding to BALB/c3T3 and p6 cells, in serum-free medium for 24 hours. The number of IGF-1 receptors in quiescent BALB/c3T3 cells was low (~8,000 per cell; panel a), while a high level of IGF-1 binding sites was observed in p6 cells (~43,000 per cell; panel b). BALB/c3T3 and p6 cells (transfected with the human IGF-1 R expression plasmid) were inoculated in serum supplemented medium, and after 24 hours, the medium was changed to serum-free medium. In some plates, the cells were left in serum-free medium, and in others, the serum-free medium was supplemented with increasing concentrations of insulin or IGF-1. Growth was measured by direct count of cell numbers. Under these conditions, neither 3T3 nor p6 cells grew in serum-free medium, indicating that all growth factors had been removed.

With IGF-1, growth of p6 cells is maximally stimulated at 50-100 μg/ml, with insulin at 20-50 μg/ml. It is generally assumed that at these concentrations the effect of insulin is largely due to its interaction with the IGF-1 receptor. Neither IGF-1 nor insulin stimulated control BALB/c3T3 cells at the concentrations used.

Antisense deoxyoligonucleotides complementary to oncogene mRNAs have been shown to be effective in inhibiting the growth of cells in culture. Therefore, this approach was used to determine the significance of IGF-1 R overexpression in the growth of p6 cells. Anti-IGF-1 R deoxyoligonucleotides were added to p6 cells in serum-free medium for 48 hours. At a concentration of 80 μg/ml, the antisense deoxyoligonucleotides inhibited IGF-1—stimulated growth by 50%, and inhibition was found to be concentration dependent. No such effect was observed when sense deoxyoligonucleotides were added to the medium. This experiment was repeated and the antisense deoxyoligonucleotide was found to inhibit growth by 40-60%, while the sense deoxyoligonucleotide had no effect. Antibody to the IGF-1 R also produced a 40% inhibition of IGF-1 mediated growth in p6 cells.

The growth of BALB/c3T3 cells and derivative cell lines p6 and p12 in serum-free medium was evaluated. The plates were coated either with calf serum or poly-D lysine. Cells were then seeded at a concentration of $2 \times 10^4$ cells/cm², and the number of cells were counted on successive days. Only p12 cells, which were transfected with both the IGF-1 and IGF-1 R plasmids, grew well in serum-free medium. There was no difference in the growth of p12 cells on the basis of whether calf serum or poly-D-lysine was used as the attachment factor. While in most experiments bovine serum albumin was added to the serum-free medium, its omission had no effect on the growth of p12 cells. Neither BALB/c3T3 nor p6 cells grew in serum-free medium, regardless of whether they were plated in serum or on poly-D-lysine.

In summary, p12 cells grew well in serum-free medium without the addition of any growth factors, but with the supplementation of an attachment factor and ferrous sulfate to replace transferrin. In contrast, p6 cells grew for about 2-3 days only under the same conditions. p12 cells could be passaged several times in serum-free medium, provided an attachment factor was used to coat the plastic dishes.

We could not detect any PDGF-like activity in the conditioned medium of p12 or p6 cells. For instance, when BALB/c3T3 cells were incubated with conditioned medium from p12 cells, (which contains abundant IGF-1) the number of cells varied from $1.5 \times 10^4$ cells/cm² on day 1, to $2.0 \times 10^4$ on day 5. Under the same conditions, addition of PDGF increased the number of cells to $6.5 \times 10^4$/cm².

We then examined the phosphorylation of the EGF receptor and phospholipase Cγ1 (PLCγ1) in both 3T3 and p6 cells. In both p6 and 3T3 cells, PDGF induced phosphorylation of the EGF receptor, and of PLCγ1. IGF-1 failed to stimulate phosphorylation of these two substrates in either p6 or 3T3 cells. Under these conditions, p6 (but not 3T3) cells enter DNA synthesis and divide.

The invention is further illustrated by the following, non-limiting examples.

EXAMPLES

Example 1 Cell Lines

BALB/c3T3 cells, transfected with a plasmid expressing the human IGF-1 R cDNA under the control of the SV40 promoter as well as the neo-resistance gene, Lammers et al., *EMBO J.*, 8:1369-1375 (1989), were selected in G418, and designated p6 cells. These cells were then super-transfected with a human IGF-1 cDNA expression plasmid, also under the control of an SV40 promoter and plasmid pLHL4, Gritz and Davies, *J. Gene*, 25:179-188 (1983), specifying hygromycin resistance. The resultant p12 cells were continuously grown in media supplemented with hygromycin (300 μg/ml) and G418 (400 μg/ml). p6 cells were grown in the presence of G418 (400 μg/ml) only. Transfections were done in suspension according to the method described by Shen et al., *Mol. Cell Biol.*, 2:1145-1154 (1982).

Example 2 Cell Cultures

All cell lines tested were passaged in DMEM medium supplemented with either 5% fetal bovine serum and 5% calf serum, or 10% calf serum only. To culture these cells in serum-free medium (SFM), DMEM was supplemented with bovine serum albumin (BSA, 0.5 mg/ml) and FeSO4 at a concentration of 1 μm. Plating in serum supplemented medium was done so as to allow cell attachment to the surface before being placed in SFM, at which time cells were washed twice with DMEM and then refed with SFM. In most experiments however, the plating in serum supplemented medium was replaced by simply coating the cover slips with poly-D-lysine (high molecular weight, Collaborative Research).

Example 3 Plasmids pCVN-IGF1-R contains a human IGF-1 receptor cDNA, fragment 1-4142 (XbaI-BamHI) under the control of the SV40 promoter. This plasmid also contains the DHFR coding sequence and Neo-R, both under the control of the SV40 promoter, Lammers et al., *EMBO J.*, 8:1369-1375 (1989); Ullrich et al., *EMBO J.*, 5:2503-2512 (1986). pCvn-IGF-1 contains a 600 bp XhoI-EcoRV cDNA fragment of human/IGF-1 under the control of an SV40 promoter. pLHL4, Gritz and Davies, *J. Gene*, 25:179-188 (1983) was used for resistance to hygromycin. The phigf I plasmid, containing in vector pKT218 a 662 bp fragment of IGF-1 cDNA, courtesy of Dr. Graeme Bell (University of Chicago), was only used as a probe. Other probes are described in the following examples.

Example 4 RNA Extraction and RNA Blots

Total RNA was extracted from cells by the method of Chomczynski and Sacchi, *Anal. Biochem.,* 162:156–159 (1987) and RNA blots were carried out by standard procedures, Thomas, P. S., *Methods Enzymol.,* 100:255–266 (1983). Radioactive probes were prepared by the Random Priming method, Feinberg and Vogelstein, *Anal. Biochem.,* 132:6–13 (1983). The following probes were used: a) IGF-1: a full length insert from the phigf I plasmid; b) IGF-1 R: a SphI fragment of the human IGF-1 receptor cDNA which is a 2.1 kb internal fragment, straddling the a and b domains, Ulrich et al., *EMBO. J.,* 5:2503–2512 (1986); and c) 3A10 probe, the insert fragment HindIII/Sal I derived from plasmid p3A10 described by Lin and Lee, *Proc. Natl. Acad.. Sci.,* 81:988–992 (1984). The mRNA from which the p3A10 insert was derived is expressed in constant amounts throughout the cell cycle and under different growth conditions, and is used to monitor the amounts of RNA in each lane.

Synthetic antisense oligonucleotide TCCTCCGGAGCCAGACTT (SEQ ID NO:1) and sense deoxyoligonucleotide AAGTCTGGCTCCGGAGGA (SEQ ID NO: 2) to codons 21-29 of the signal sequence of the subunit of IGF-1 R preceding the proreceptor sequence, Ulrich et al., *EMBO J.,* 5:2503–2512 (1986), were synthesized on an Applied Biosystem Inc., Model 391 EP DNA synthesizer using β-cyanoethyl phosphormamidite chemistry. These oligonucleotides were added to cultures of p6 cells 24 hours after plating.

Example 5 $I^{125}$-IGF-1 Binding

Recombinant human IGF-1 was from IMCERA (Mallinckrodt St. Louis, Mo.). IGF-1 binding was carried out as previously described in Phillips et al., *J. Cell Physiol.,* 133:135–143 (1987). Briefly, BALB/c3T3 cells and p6 cells were seeded into 24 well plates and grown in 10% FBS-containing medium for 2 to 4 days. The cultures were then stepped down into serum free medium MCDB-104 (NaHCO3 buffered) containing 1 mg/ml BSA. Binding assays were done 24–48 hours later. The cultures were then incubated with 0.1–0.5 nM $I^{125}$-IGF-1 in binding medium MCDB-104 (Hepes buffered) containing 1 mg/ml BSA in the absence or presence of graded concentrations of unlabeled IGF-1. Triplicate wells were used for all data points. After 2.5 hours at 4° C., the cells were rinsed two times with ice-cold binding medium and solubilized in 0.01N NaOH, 0.1% Triton X-100, 0.1% SDS. An aliquot from each well was counted in a Packard liquid scintillation counter. Non-specific binding was defined as radioactivity that remained bound in the presence of a 400 fold molar excess of unlabeled IGF-1. IGF-1 was iodinated to an activity of 50–250 mCi/mg, as previously described. Cell numbers were determined from triplicate wells which were manipulated the same as those wells used for the binding measurements.

Example 6 Phosphorylation of PLCγ1 in IGF-1 Transfected Cells In Response to IGF-1

Three 100 mm dishes each of BALB/c3T3 and p6 cells (approximately 70% confluent) were refed with 1.5 ml phosphate-free MEM containing 0.5% dialyzed calf serum. 2 mCi-$^{32}$p orthophosphate (ICN Biochemicals) were added, per dish, and incubated at 37° for 4 hours. 15 minutes before the end of labelling, 50 ng/ml PDGF or IGF-1 were added to one dish of each set. At the end of labelling, the dishes were placed on ice and washed 4× with 2 ml cold CMF-PBS (calcium- and magnesium-free phosphate buffered saline). Cells from each dish were scraped into 1 ml RIPA buffer (0.15M NaCl, 10 mM Tris, pH 7.4, 1% Triton X-100, 1% sodium deoxycholate, 0.1% sodium dodecylsulfate, 1 mM ethylenediamine tetraacetic acid, 100 KIU/ml aprotinin) containing 1 mM phenylmethyl sulfonyl fluoride, 1 mM sodium orthovanadate, and 20 mM β-glycerophosphate, incubated on ice for 20 minutes, then centrifuged at 100,000× g for 30 minutes to remove insoluble material. Cell extracts were precleared by incubation for 2 hours at 4° with 30 μl normal rabbit serum and 30 μl Pansorbin (formalin-fixed Staphylococcus A cells, Calbiochem). EGF receptors and PLCγ1 were sequentially immunoprecipitated from each precleared extract. For immunoprecipitation of EGF receptors, the extracts were incubated for 2 hours at 4° with 3 μl anti EGF-R serum #986, Stoscheck and Carpenter, *Arch. Biochem. Biophys.,* 227:457–468 (1983), and 30 L Pansorbin. For immunoprecipitation of P1-Cγ1, the supernatants of the EGF-R precipitation were incubated with 3 μl anti PLC 1 serum #101, Arteaga et al., *Proc. Natl. Acad. Sci. USA,* in press (1991), overnight at 4°, followed by incubation with 30 l Pansorbin for 30 minutes at 4°. Pansorbin pellets in each case were washed 4× with 370 RIPA buffer adjusted to pH 8.5. The washed Pansorbin pellets were mixed with 100 μl Laemmli sample buffer, Laemmli, U. K., *Nature,* 227:680–685 (1970), heated to 60° for 5 minutes, then spun in a microfuge for 2 minutes. The samples were run on a 7.5% SDS-polyacrylamide gel along with unlabelled molecular weight markers (BRL), and the dried, Coomassie stained gel was exposed overnight to Kodak X-OMAT film at −70° in the presence of intensifying screens.

Example 7 Growth Factors

For stimulation experiments, recombinant IGF-1 was identical to that used for binding studies. Insulin was from Sigma.

---

What is claimed is:

1. Cultured mammalian cells selected from the group consisting of BALB/c 3T3, CHO and tk-ts 13 cells which have been transfected with and constitutively express IGF-1 and IGF-1 receptor cDNAs and are able to grow in serum free media without the addition of exogenous growth factors that are required by the untransfected parent cell lines.

2. Method of producing a selected heterologous protein by transfecting said cultured mammalian cells of claim 1 with a recombinant DNA molecule encoding a selected heterologous protein under the control of a suitable expression control sequence, and culturing the transfected cells in suitable, serum-free culture conditions without the addition of growth factors to produce the selected heterologous protein.

3. The method of claim 2 wherein the cultured mammalian cells are tk-ts 13 cells and they are cultured at 39.6° C.

* * * * *

UNITED STATES PATENT AND TRADEMARK OFFICE
CERTIFICATE OF CORRECTION

PATENT NO. : 5,262,308

DATED : November 16, 1993

INVENTOR(S) : Renato Baserga

It is certified that error appears in the above-identified patent and that said Letters Patent is hereby corrected as shown below:

In Column 2, line 20, before "poor", insert -- growth factors are usually necessary for growth. For, instance, platelet derived growth factor (PDGF) and platelett --

In Column 3, line 42, after "IGF-", change "I" to -- 1 --

In Column 4, line 58, after "It", change "in" to -- is --

In Column 7, line 33, after "IGF-1 R", insert -- mRNA --

Signed and Sealed this

Twenty-first Day of June, 1994

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 18

(B) TYPE: Nucleic acid
(C) STRANDEDNESS: Single
(D) TOPOLOGY: Linear (iv) ANTI-SENSE: Yes (xi) SEQUENCE DESCRIPTION: SEQ ID NO: 1:

```
TCCTCCGGAG CCAGACTT                    18
```

(2) INFORMATION FOR SEQ ID NO: 2:

(i) SEQUENCE CHARACTERISTICS:
(A) LENGTH: 18
(B) TYPE: Nucleic acid
(C) STRANDEDNESS: Single
(D) TOPOLOGY: Linear (iv) ANTI-SENSE: No (xi) SEQUENCE DESCRIPTION: SEQ ID NO: 2:

```
AAGTCTGGCT CCGGAGGA                    18
```